US008491305B2

(12) United States Patent
Pogorelsky

(10) Patent No.: US 8,491,305 B2
(45) Date of Patent: *Jul. 23, 2013

(54) SYSTEM AND METHOD FOR ALIGNING TEETH

(76) Inventor: Yan Pogorelsky, Miller Place, NY (US)

( * ) Notice: Subject to any disclaimer, the term of this patent is extended or adjusted under 35 U.S.C. 154(b) by 552 days.

This patent is subject to a terminal disclaimer.

(21) Appl. No.: 12/612,794

(22) Filed: Nov. 5, 2009

(65) Prior Publication Data

US 2011/0104639 A1    May 5, 2011

(51) Int. Cl.
*A61C 13/10*    (2006.01)
(52) U.S. Cl.
USPC ........................................................... 433/193
(58) Field of Classification Search
USPC .................. 433/193, 53–74, 172–176, 201.1, 433/194, 191
See application file for complete search history.

(56) References Cited

U.S. PATENT DOCUMENTS

| 1,780,117 | A |   | 10/1930 | Craigo |
|---|---|---|---|---|
| 4,060,899 | A | * | 12/1977 | Sauter ............................. 433/74 |
| 4,371,340 | A | * | 2/1983 | Imaizumi ........................ 433/74 |
| 4,767,331 | A |   | 8/1988 | Hoe |
| 4,801,264 | A | * | 1/1989 | Weissman ....................... 433/74 |
| 5,286,191 | A |   | 2/1994 | Poveromo |
| 5,752,831 | A | * | 5/1998 | Padros-Fradera ............. 433/173 |
| 5,788,489 | A |   | 8/1998 | Huffman |
| 5,788,494 | A | * | 8/1998 | Phimmasone ................ 433/213 |
| 5,975,893 | A |   | 11/1999 | Chishti |
| 6,217,325 | B1 |   | 4/2001 | Chishti |
| 6,299,440 | B1 |   | 10/2001 | Phan |
| 6,318,994 | B1 |   | 11/2001 | Chishti |
| 6,390,812 | B1 |   | 5/2002 | Chishti |
| 6,394,801 | B2 |   | 5/2002 | Chishti |
| 6,398,548 | B1 |   | 6/2002 | Muhammad |
| 6,406,292 | B1 |   | 6/2002 | Chishti |
| 6,450,807 | B1 |   | 9/2002 | Chishti |
| 6,457,972 | B1 |   | 10/2002 | Chishti |
| 6,471,511 | B1 |   | 10/2002 | Chishti |

(Continued)

FOREIGN PATENT DOCUMENTS

| KR | 10-2002-0080305 | 2/1994 |
|---|---|---|
| RU | 2223716 | 2/2004 |

OTHER PUBLICATIONS

O.I. Arsenina et al. Diagnostics and planning of orthodontic treatment of patients with crowded teeth position with the use of elastomeric correction splints. Stomatologiia (Mosk) 2011; 2:78.

(Continued)

*Primary Examiner* — Cris L Rodriguez
*Assistant Examiner* — Mirayda A Aponte
(74) *Attorney, Agent, or Firm* — Leason Ellis LLP

(57) ABSTRACT

A dowel pin and sleeve combination for use with a tooth die that is part of a dental model includes a dowel pin and a sleeve that receives the pin. The dowel pin includes a tooth anchor section that is configured to be fixedly attached to the tooth die and a main body section having a bore formed therein. The main body section has a living hinge formed therein that partitions the main body section into an upper pivotable portion that pivots about the hinge and a lower portion. A section of the bore is threaded and the main body section includes an urging member that travels along the threaded bore section and can be driven into contact with the pivotable portion of the main body section.

13 Claims, 7 Drawing Sheets

U.S. PATENT DOCUMENTS

| | | |
|---|---|---|
| 6,485,298 B2 | 11/2002 | Chishti |
| 6,499,997 B2 | 12/2002 | Chishti et al. |
| 6,554,611 B2 | 4/2003 | Chishti |
| 6,582,227 B2 | 6/2003 | Phan |
| 6,602,070 B2 | 8/2003 | Miller |
| 6,626,666 B2 | 9/2003 | Chishti |
| 6,629,840 B2 | 10/2003 | Chishti |
| 6,685,469 B2 | 2/2004 | Chishti |
| 6,699,037 B2 | 3/2004 | Chishti |
| 6,705,861 B2 | 3/2004 | Chishti |
| 6,722,880 B2 | 4/2004 | Chishti |
| 6,729,876 B2 | 5/2004 | Chishti |
| 6,761,560 B2 | 7/2004 | Miller |
| 6,767,208 B2 | 7/2004 | Kaza |
| 6,783,360 B2 | 8/2004 | Chishti |
| 6,786,721 B2 | 9/2004 | Chishti |
| 6,802,713 B1 | 10/2004 | Chishti |
| 7,037,108 B2 | 5/2006 | Chishti |
| 7,037,111 B2 | 5/2006 | Miller |
| 7,063,533 B2 | 6/2006 | Phan |
| 7,074,038 B1 | 7/2006 | Miller |
| 7,077,647 B2 | 7/2006 | Choi |
| 7,108,508 B2 | 9/2006 | Hedge |
| 7,156,661 B2 | 1/2007 | Choi |
| 7,192,275 B2 | 3/2007 | Miller |
| 7,220,122 B2 | 5/2007 | Chishti |
| 7,247,021 B2 | 7/2007 | Jones |
| 7,261,533 B2 | 8/2007 | Wrosz |
| 7,273,367 B2 | 9/2007 | Huges |
| 7,293,988 B2 | 11/2007 | Wen |
| 7,326,051 B2 | 2/2008 | Miller |
| 7,331,783 B2 | 2/2008 | Chishti |
| 7,335,024 B2 | 2/2008 | Wen |
| 7,377,778 B2 | 5/2008 | Chishti |
| 7,435,083 B2 | 10/2008 | Chishti |
| 7,476,100 B2 | 1/2009 | Kuo |
| 7,578,674 B2 | 8/2009 | Chishti |
| 7,600,999 B2 | 10/2009 | Knopp |
| 2002/0094503 A1 | 7/2002 | Chishti |
| 2003/0207227 A1 | 11/2003 | Abolfathi |
| 2003/0211440 A1 | 11/2003 | Kuo |
| 2004/0019723 A1* | 1/2004 | Ostrovsky et al. ............ 710/260 |
| 2004/0166456 A1 | 8/2004 | Chishti |
| 2004/0166462 A1 | 8/2004 | Phan |
| 2004/0166463 A1 | 8/2004 | Wen |
| 2004/0170941 A1 | 9/2004 | Phan |
| 2004/0202983 A1 | 10/2004 | Tricca |
| 2004/0243361 A1 | 12/2004 | Steuben |
| 2005/0055118 A1 | 3/2005 | Nikolskiy |
| 2005/0106525 A1 | 5/2005 | Knopp |
| 2005/0233278 A1 | 10/2005 | Kim |
| 2005/0244782 A1 | 11/2005 | Chishti |
| 2006/0003283 A1 | 1/2006 | Miller |
| 2006/0084030 A1 | 4/2006 | Phan |
| 2006/0222474 A1* | 10/2006 | Brown et al. ................. 411/340 |
| 2006/0233278 A1* | 10/2006 | Zerbe et al. ................... 375/286 |
| 2007/0015105 A1* | 1/2007 | Campanello .................... 433/74 |
| 2007/0065771 A1* | 3/2007 | Kohani ........................... 433/74 |
| 2007/0092850 A1 | 4/2007 | Kaza |
| 2008/0020337 A1 | 1/2008 | Phan |
| 2008/0020340 A1 | 1/2008 | Matov |
| 2008/0166676 A1 | 7/2008 | Chishti |
| 2008/0182221 A1 | 7/2008 | Chishti |
| 2008/0187879 A1 | 8/2008 | Chishti |
| 2008/0280258 A1 | 11/2008 | Wen |
| 2009/0298017 A1 | 12/2009 | Boerjes et al. |
| 2010/0151404 A1 | 6/2010 | Wu |
| 2011/0104639 A1 | 5/2011 | Pogorelsky |
| 2011/0104640 A1 | 5/2011 | Pogorelsky |

OTHER PUBLICATIONS

Altan Varol et al. The role of computer-aided 3D surgery and stereolithographic modelling for vector orientation in premaxillary and trans-sinusoidal maxillary distraction osteogenesis. Int J Med Robotics Compr Assist Surg 2009; 5:198-206.

* cited by examiner

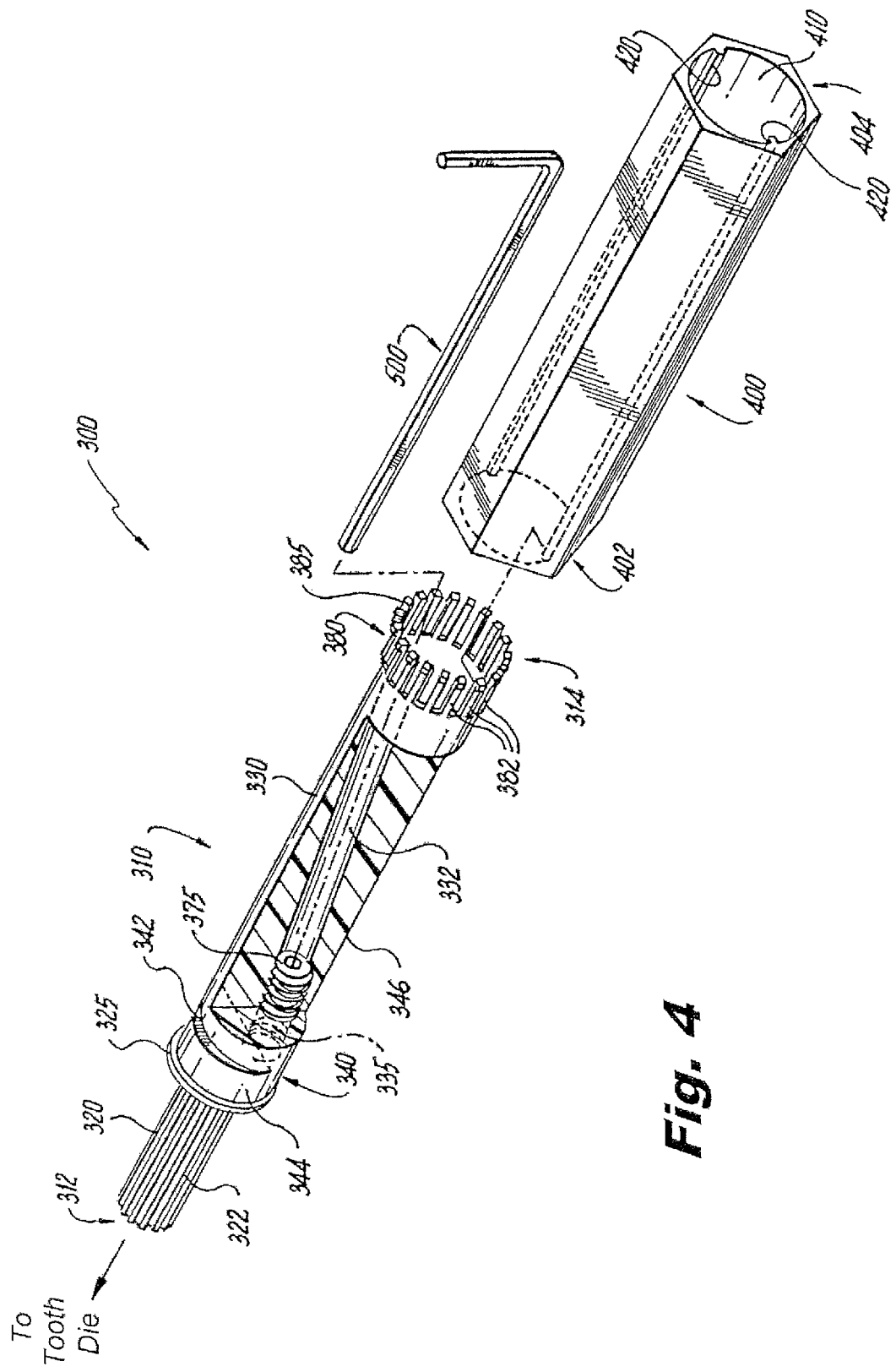

SYSTEM AND METHOD FOR ALIGNING TEETH

TECHNICAL FIELD

The present invention relates to orthodontics and in particular, the present invention relates to a system and method for incrementally moving one or more teeth from an initial tooth arrangement to a final tooth arrangement.

BACKGROUND

Orthodontics is a specialty of dentistry that is concerned with the study and treatment of malocclusions (improper bites) which can be a result of tooth irregularity, disproportionate jaw relationships, or both. Orthodontic treatment can focus on dental displacement only and can be carried out for purely aesthetic reasons with regard to improving the general appearance of patient's teeth. However, there are other orthodontic treatments that are more complex and are needed to reconstruct the face. This type of treatment is most often prescribed for practical reasons such as providing the patient with a functionally improved bite (occlusion).

Conventionally, repositioning teeth for aesthetic reasons or other reasons is accomplished by wearing a device that is commonly referred as dental braces. Dental braces are formed of a variety of appliances such as brackets, archwires, ligatures, and O-rings. Attaching dental braces to the teeth of a patient is a tedious, time consuming task that requires a number of meetings between the patient and orthodontist to first prepare and fit the dental braces and then make necessary adjustments to the dental braces. Before the braces are fixedly attached to the patient's teeth, various molds and fittings are required in order to formulate the strategy. To attach the braces, a weak acid is first applied to the teeth to increase the adherence of the braces to the teeth. Brackets and bands that form the dental braces are bonded to the patient's teeth using cement.

The primary force-inducing appliance in a conventional set of braces is the archwire. The archwire is resilient and is attached to the brackets by way of slots in the brackets. The archwire links the brackets together and exerts forces on them to move the teeth over time. After the archwire is in place, periodic meetings with the orthodontist are required and during these meetings, the patient's braces are adjusted by installing a different archwire having different force-inducing properties or by replacing of tightening existing ligatures.

Besides being a time consuming process, conventional braces are also very unsightly and are uncomfortable to wear to the presence of these components in the mouth, bonded to and extending across the teeth, etc.

In recent years, improvements in the field of orthodontistry have produced dental products that are alternatives to conventional braces. For example, a dental system available under the name "Invisalign®" is distributed by Align Technologies. This system involves a process where, once a candidate is found to be suitable for wearing this type of product, impressions and pictures of the patient's teeth are taken. The teeth impressions are digitized and sent to the company to establish a plan for tooth movement over a treatment timeline which is typically 18 months. Based on a precise treatment plan, customized aligners are created for the patient to wear at each stage of the treatment. Typically, a full set of treatment includes 20-30 aligners per arch. The aligners are worn as much as possible, with the exception of eating and drinking, in order to complete the treatment within the timeline established with the patient.

The Invisalign® system is a computer based system in which not only are the imprints digitized and stored in memory but also the computer uses algorithms and the like to develop virtual correction steps (i.e., incremental changes in the teeth to be implemented over months or years). After the virtual correction steps are calculated, a sophisticated laser machining of multiple adjusters controlled by the same computer. Therefore, the production is expensive and a complete set of braces is made in advance and corrective interaction during the treatment process is practically not feasible.

The Invisalign® system is fairly costly to patients and also the plan is designed to be implemented over a long time period. As a result, the patients typically wear a particular aligner for a single month and due to the substantial number of aligners that are used, the process is implemented over a substantial number of months. For example, the patient is given a tray of about 20 aligners which are used by the patient over the next 20 successive months.

Due to certain limitations of the Invisalign® system, some of which are described herein, the course of treatment is spread out over many months as a result of the slight incremental changes that are incorporated into the aligners. For example, the Invisalign® system uses a laser incorporated as part of a vacuum forming machine that is used to heat and thereby form the aligner and, therefore, the thickness of the vacuum forming material is limited to thicknesses that can be processed with the laser without destroying the material. This imposes a limitation on the manufacturing process as well as the treatment time table that can be proposed to a patient.

While the Invisalign® system has merit, it would be advantageous to provide a system that is model that has a plurality of tooth dies is provided.

SUMMARY

At least one tooth die can be selectively adjusted to a new position to allow formation of an aligner that is intended to be worn on teeth of the patient. The model includes a first model part that is formed of a plurality of tooth dies and a second model part complementary to the first model part and being in the form of a base that supports the tooth dies. The model further includes a dowel pin and sleeve combination for use with the tooth die that is intended to be adjusted. The combination includes a dowel pin including a tooth anchor section that is configured to be fixedly attached to the tooth die and a main body section having a bore formed therein and open at one end of the pin. The main body section has a slot that defines a living hinge formed therein that partitions the main body section into an upper pivotable portion that pivots about the hinge and a lower portion. A section of the bore is threaded and the main body section includes an urging member that travels along the threaded bore section and can be driven into contact with the pivotable portion of the main body section. The bore forms an entrance into the slot that defines the living hinge to permit the urging member to be driven into contact with the pivotable portion. The pin also includes a gear section that is located at an end of the main body section opposite the tooth anchor section. The gear section has teeth with the bore extending through the gear section so as to be open at the one end of the pin. The combination also includes a sleeve for fixation in a base of the model. The sleeve has a central bore formed therein that is configured to receive the pin and permit the pin to be rotated therein. The central bore includes a longitudinal locating and locking rail formed therein. The rail has dimensions that permit it to lockingly engage the teeth of the gear section.

The tooth die is pivotable about the living hinge and can be rotatable relative to the sleeve.

The physical 3-D model of the patient's teeth allows the orthodontist to individually adjust those tooth dies that require adjustment as part of the treatment plan. The model is used in combination with conventional dentist equipment (e.g., vacuum forming equipment) to construct aligners that are used to adjust the patient's tooth in an incremental manner from an initial tooth arrangement to a desired, final tooth arrangement. The present system provides a number of advantages and a degree of customization not available with the conventional computer-based systems.

These and other aspects, features and advantages shall be apparent from the accompanying Drawings and description of certain embodiments of the invention.

BRIEF DESCRIPTION OF THE DRAWINGS

FIG. 4 is an exploded perspective view of a dowel pin assembly in accordance with the present invention;

DETAILED DESCRIPTION OF CERTAIN EMBODIMENTS OF THE INVENTION

In accordance with one embodiment of the present invention, systems and methods are provided for incrementally moving one or more teeth using a plurality of discrete members (aligners) that successively move one or more teeth by predetermined amounts. The system is configured so that the tooth movements are those normally associated with orthodontic treatment, including translation in all three orthogonal directions relative to a vertical centerline, rotation of the tooth centerline in the two orthodontic directions ("root angulation" and "torque"), as well as rotation about the centerline. These movements are shown in FIG. 1.

As described herein and in contrast to the computer-based systems of the conventional systems described above, the system and method of the present invention avoid the complexity of the computer-based systems and provide a more personal treatment plan that can be discussed and developed directly between the patient and his or her orthodontist. The present invention generally is in the form of an adjustable dowel pin assembly that support tooth dies and are embedded into a physical 3-D model of the patient's teeth to allow the orthodontist to individually adjust those tooth dies that require adjustment as part of the treatment plan. The model is used in combination with conventional dentist equipment (e.g., vacuum forming equipment) to construct aligners that are used to adjust the patient's tooth in an incremental manner from an initial tooth arrangement to a desired, final tooth arrangement. The present system provides a number of advantages and a degree of customization not available with the conventional computer-based systems.

Figure 1:
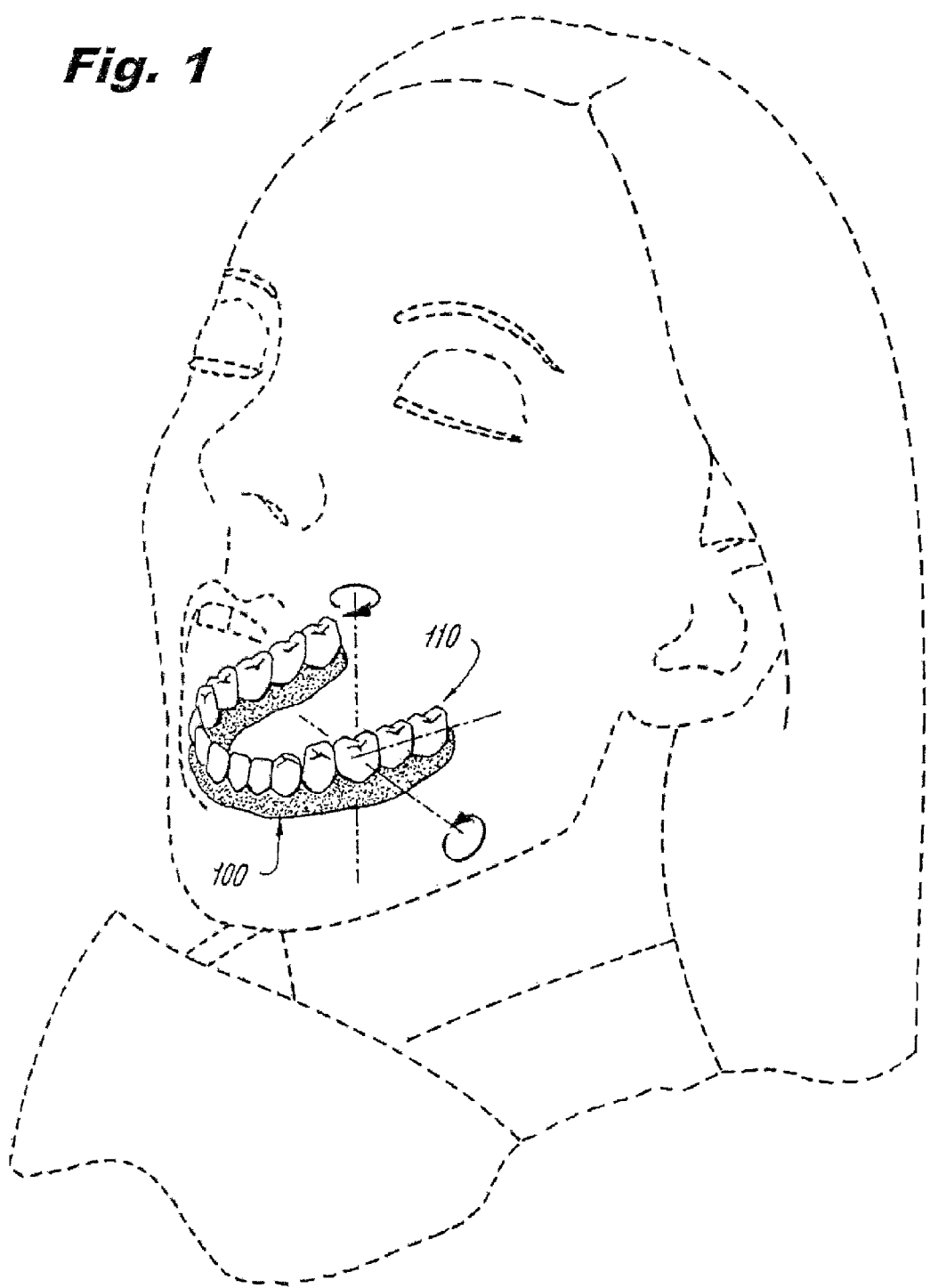
FIG. 1 illustrates a patient's jaw and provides a general indication of how teeth can be moved in accordance with the system and method of the present invention.

FIG. 1 shows a representative jaw 100 that includes sixteen teeth 110. The present invention is intended to move at least some of these teeth 110 from an initial tooth arrangement to a final tooth arrangement.

Figure 2:
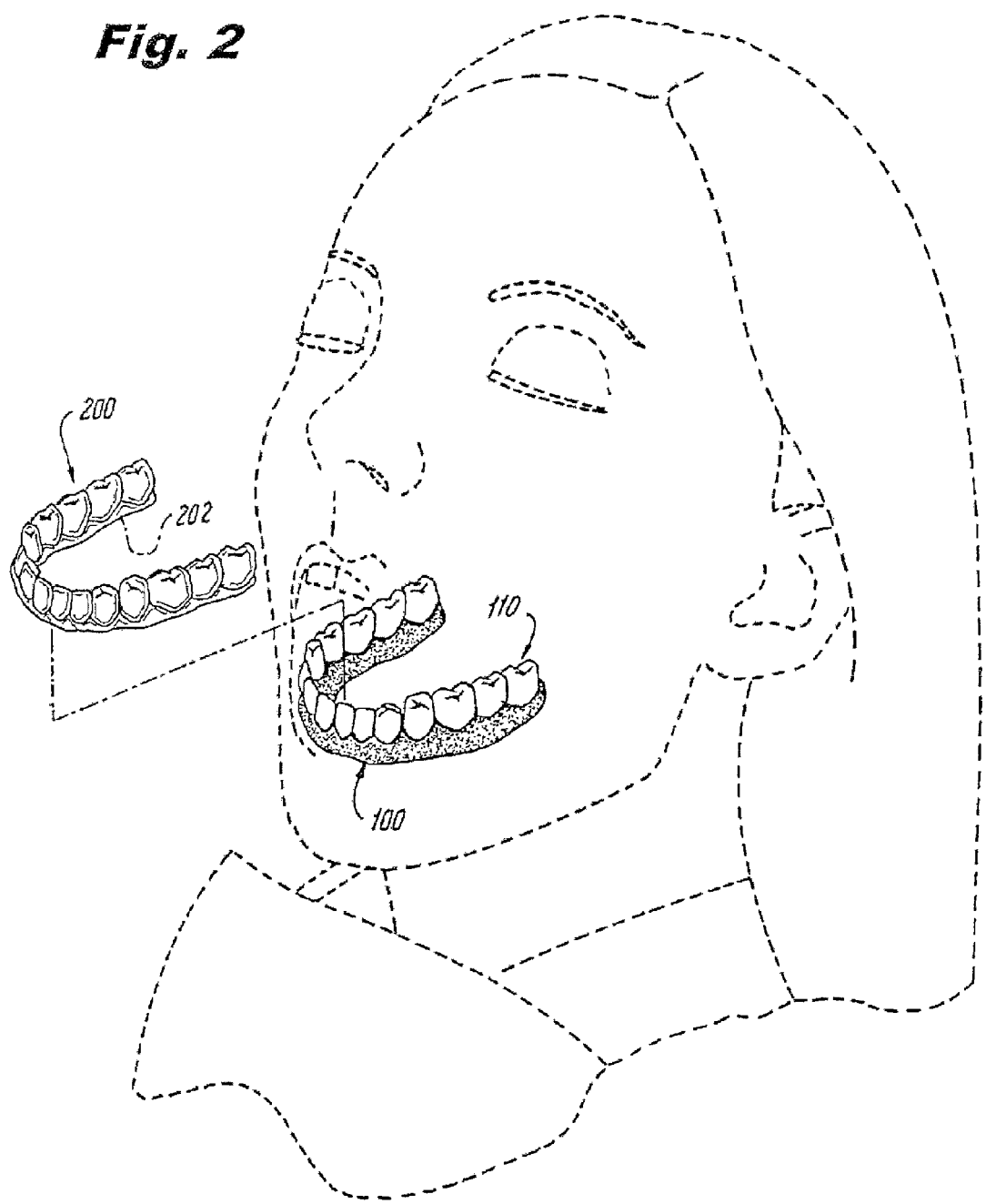
FIG. 2 illustrates the jaw of FIG. 1 with an incremental position adjustment device that has been configured for placement over the teeth to cause over time incremental movement of the teeth.

FIG. 2 is a perspective view of a discrete member or apparatus (teeth positioner or aligner) 200 that is part of the system of the present invention and is intended to cause the movement of one or more teeth. In order to move the one or more target teeth from the initial tooth arrangement to the final tooth arrangement, one to a plurality of aligners 200 are used over a prescribed period of time determined by the orthodontist. Each aligner is intended to effect incremental repositioning of individual teeth in the jaw as described above. When plural aligners 200 are created for a given patient, they are intended to be worn successively by the patient in order to achieve gradual tooth repositioning as described below in greater detail. An exemplary aligner 200 is formed of a polymeric shell that has a cavity 202 shaped to receive and resiliently reposition teeth from one tooth arrangement to a successive tooth arrangement. Typically, the polymeric shell fits over all teeth present in the upper or lower jaw; however, this is not an absolute requirement and other arrangements are possible. Many times, only certain teeth are repositioned while other teeth will provide a base or anchor region for holding the aligner 200 in place as it applies the resilient repositioning force against the tooth or teeth to be repositioned.

The aligner 200 is formed from a sheet of a suitable elastomeric polymeric and more particularly, the aligner 200 is formed from a sheet of dental material. For example, the aligner can be formed a vacuum forming material that is used in the dental field and is available from a number of different commercial suppliers. In one embodiment, the aligner is formed of a vacuum forming material that is available is sheets of varying thicknesses from Henry Schein. For example, the sheets of vacuum forming material can come in thicknesses of 0.60", 0.80", 0.10" and 0.12". It will be appreciated that that these sheet thicknesses are substantially greater than the 0.02" thickness of the material that is used to form the dental appliances used in the Invisalign® system, and as such are more rigid and so they are able to impact a greater movement of teeth than possible using a thinner aligner such as in the Invisalign® system.

As described in detail below, the aligner 200 is intended to be worn over teeth without for wires or other attachment means being used and instead, the aligner 200 is constructed to hold the aligner 200 in place over the teeth without such external assistance.

Figure 3:
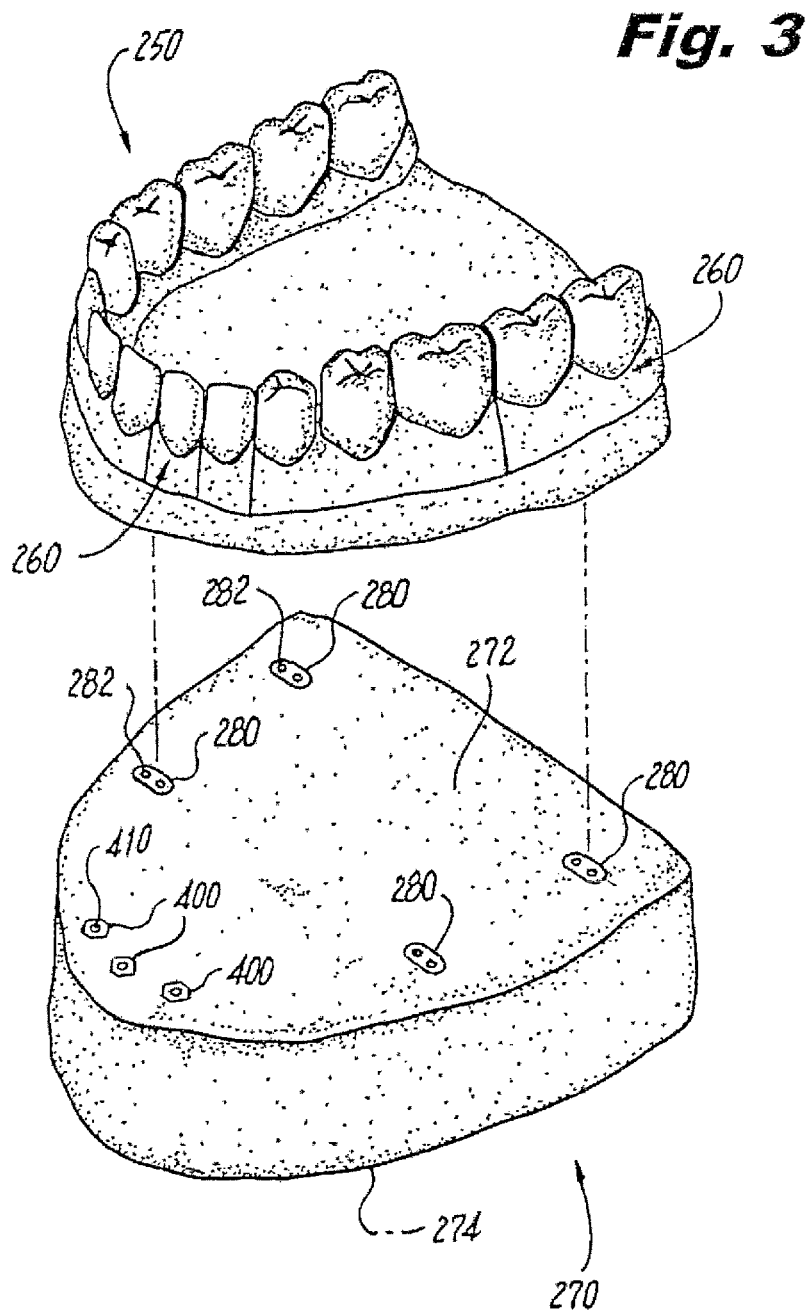
FIG. 3 is a top perspective view of an adjustable dental model in accordance with the present invention showing a tooth die(s) portion and a base portion.

Now referring to FIGS. 2-4, an exemplary system and method of the present invention are shown.

In accordance with one embodiment of the present invention, a dental impression of the patient's teeth is first formed. As is known in the art, a dental impression is an accurate representation of part or all of a person's dentition and other areas of the mouth. From an imprint of a person's teeth and gums in wax or plaster, a dental impression forms a "negative" of those teeth and gums. The negative is then used to make a cast or model 250 of the dentition, which is also called a die and represents a positive replica of the tooth or teeth. An exemplary model 250 is shown in FIG. 3. The impression is carried out by placing a viscous liquid material into the mouth usually in a customized tray. The material then sets to become an elastic solid and when removed from the mouth retains the shape of the teeth. Common materials used for dental impression are sodium alginate, polyether and silicones (both condensation-cured silicones and addition-cured silicones, such as polyvinyl siloxane.

After forming the model 250 of the patient's teeth in the initial tooth arrangement, it is often desirable and typically necessary to separate one tooth die 260 from the remainder of the model of the patient's mouth. Any number of conventional techniques can be used to separate one tooth die 260 from the remainder of the model 250. For example, a cutting element can be used to separate each tooth die and in particular, the cutting element can be in the form of a mechanical cutting device, such as a saw, or it can be in the form of a laser that makes precise cuts. In order to permit the separated tooth die 260 to be replaced in its original relative position and orientation, the tooth dies 260 are provided with a dowel pin.

In accordance with the present invention, a device is used to form one or more openings in an underside of the tooth die in order to allow coupling of the dowel pin to the tooth die (not shown). For example, a pin indexing or pinsetter device can be used to locate dowel pin openings. As is known, the pinsetter device offers precision die pinning featuring a laser light beam indicator for easier, more accurate dowel pin location. One exemplary pinsetting machine is commercially available from Coltene/Whaledent under the trade name Pindex Mark II Laser. The pinsetter device is thus used in the model and die fabrication process of the present invention and includes a small laser beak that makes drill hole positioning more accurate. It will thus be appreciated that the Pindex machine or the like is used to precisely drill holes in the model/die that permit each separated tooth die to be removed and replaced relative to the remained of the model.

After forming the openings (dowel pin holes) in the tooth die, a shank of the dowel pin is inserted into the respective pin opening formed in the tooth die and is secured thereto using conventional techniques. For example, an adhesive, bonding material or the like, can be used to secure the shank of the dowel pin to the tooth die. The shaft of the dowel pin extends below the underside of the tooth die.

The tooth die model 250 also includes a base 270 to which the tooth dies are removably coupled. The base 270 has a top planar surface 272 and a bottom planar surface 274 so that it can rest on a support surface, such as a table or the like. The base 270 includes metal sleeves 280 which has one or more openings 282 that receive the shafts of the pins to allow coupling between the tooth dies 260 and the base 270. The metal sleeve 280 includes openings that receive the shafts of the pin.

The base 270 is formed using conventional techniques and once the pin locations are determined and the pins are inserted into the tooth dies 260, the base 270 is formed around the metal sleeves 280 and pin couplings. In this manner, the base 270 is complementary to the tooth dies 260 in that the pins of the tooth die 260 are received within complementary openings formed in the base 270 (e.g., the metal sleeves fixedly attached within the base). In this manner, the tooth dies 260 can be return to the base 270 and all the tooth dies 260 are maintained in their proper position despite being cut and being separate from adjacent tooth dies. FIG. 3 shows the base 270 containing a predetermined number of conventional metal sleeves 280 as well as sleeves that are made in accordance with the present invention as discussed below.

Figure 6:
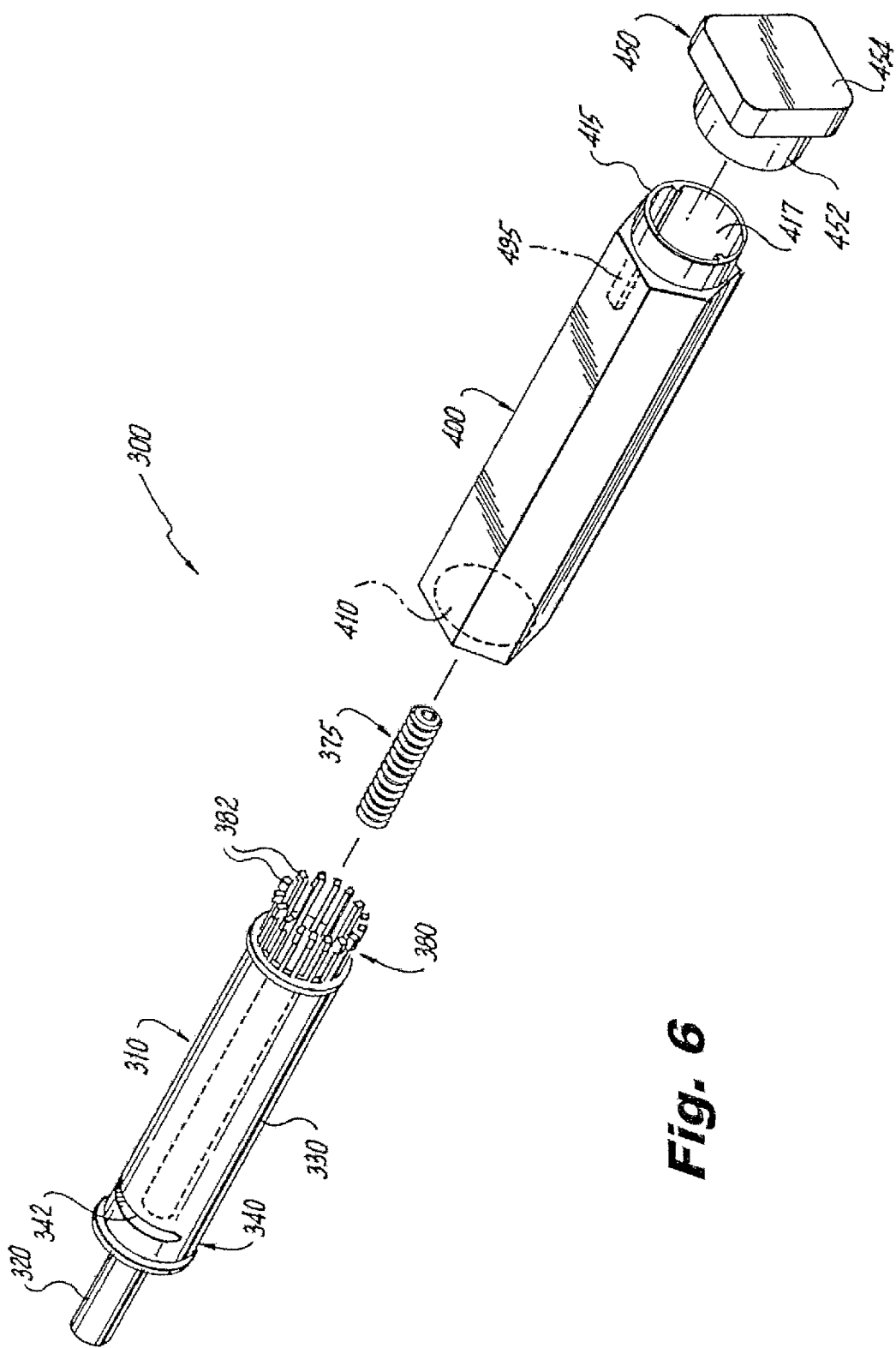
FIG. 6 is an exploded view of one exemplary dowel pin assembly according to one embodiment.

In accordance with the present invention, an adjustable dowel pin assembly 300 is provided and is best shown in FIGS. 4 and 6. The adjustable dowel pin assembly 300 is intended to be used with a tooth die 260 (FIG. 3) that is associated with one or more teeth that are to be incrementally moved during the course of treatment. FIG. 6 is an exploded view of the dowel pin assembly 300.

FIG. 4 shows one exemplary dowel pin assembly 300 that is formed of two distinct, complementary parts. More particularly, the assembly 300 includes a pin 310 and a complementary sleeve 400. As described herein, a portion of the pin 310 is fixedly attached to the tooth die and another portion of the pin 310 that extends below the tooth die is for insertion into the sleeve 400 that is fixedly coupled to the base of the model.

The sleeve 400 is an elongated member that has a first end 402 and an opposing second end 404. The sleeve 400 is a hollow member and therefore includes a bore 410 formed therethrough. The bore 410 is open at both the first end 402 and the second end 404. The sleeve 400 can have any number of different shapes. In the illustrated embodiment, the sleeve 400 has a hexagonal shaped outer surface; however, the bore 410 can have a different shape and in the illustrated embodiment, the bore 410 is circular shaped. In accordance with the present invention, the sleeve 400 has a locating and coupling element 420 that is formed within the bore 410. The coupling element 420 is in the form of a rail that runs the length of the bore 410 from the first end 402 to the second end 404. More specifically, as shown in FIG. 4, the coupling element 420 is in the form of a pair of rails 420 that are located opposite one another (180 degrees apart).

The pin 310 is likewise an elongated structure that has a first end 312 and an opposing second end 314 with the first end 312 being the end that is fixedly coupled to the tooth die and the second end 314 being the end that is coupled to the sleeve 400. The pin 310 is actually formed of a number of distinct sections, namely a tooth anchor section 320, a main body 330 and a gear section 380. The tooth anchor section 320 is located at the first end 312, the gear section 380 is located at the second end 314 and the main body 330 is an intermediate section located between the two other sections.

The tooth anchor section 320 represents the portion of the pin 310 that is inserted into the drill hole formed in the underside of the tooth die and therefore the tooth anchor section 320 is received within the tooth die and fixedly attached thereto. The tooth anchor section 320 can have a contoured or modified outer surface 322 to assist in fixedly attaching the pin 310 to the tooth die. For example, the outer surface 322 can be serrated or can have other surface modifying structures. In the illustrated embodiment, the outer surface 322 is a ribbed surface formed of a plurality of vertically oriented ribs (e.g., ribs that run longitudinally along the length of the tooth anchor section 320.

The tooth anchor section 320 can have any number of different shapes; however, the shape of the tooth anchor section 320 is complementary to the shape of the drill hole since the tooth anchor section 320 is received within the drill hole. In the illustrated embodiment, the tooth anchor section 320 has a cylindrical shape.

The anchor section 320 extends beyond the main body section 330 and therefore represents a post or the like. The anchor section 320 is preferably a solid structure to increase the integrity and strength of the connection between the pin 310 and the tooth die.

The main body section 330 is not a solid structure but rather the main body section 330 has a bore 332 formed therein. The main body section 330 can have any number of different shapes; however, the shape of the main body section 330 is complementary to the shape of the bore 410 formed in the sleeve 400 since at least a portion of the main body section 330 is disposed within the sleeve 400. In the illustrated embodiment, the main body section 330 has a cylindrical shape. In addition, the width (diameter) of the main body section 330 is greater than the width (diameter) of the tooth anchor section 320. As a result, a shoulder 325 is formed between one end of the main body section 330 and the tooth anchor section 320. The shoulder 325 has an annular shape. Optionally, the tooth anchor section 320 can be bonded as by an epoxy or cement to a tooth with the bond being between the tooth and the shoulder 325.

In accordance with the present invention, the main body section 330 has a living hinge 340 formed therein. The living hinge 340 is located proximate the end of the main body section 330 that interfaces with the tooth anchor section 320. The living hinge 340 is thus in the form of a cut or slot 342 that is formed in main body section 330. This slot 342 partitions the main body section 330 into a first part 344 that is located above the slot and extends toward the tooth anchor section 320 and a second part 346 that is located below the slot and extends toward the gear section 380. The living hinge 340 allows for relative movement between the first and second parts 344, 346. The slot 342 is thus a wedged shaped cut.

The main body section 330 has the bore 332 formed therein. The bore 332 extends along the longitudinal axis of the main body section 330. The bore 332 is open at one end of the pin 300, while the other end of the bore 332 forms an entrance into the slot 342. In other words, the bore 332 is open and accessible at the end of the pin 300 that includes the gear section 380. The bore 332 itself can have any number of different shapes and in the illustrated embodiment, the bore 332 has a circular or hexagonal shape. At least a portion 335 of the bore 332 is in the form of a threaded bore. In other words, a section 335 of the bore 360 is threaded. The section 335 is formed at one end of the bore 332 and in particular, the section 335 is formed at the end of the bore 332 that forms an entrance into the slot 342.

The main body section 330 also includes an urging member 375 that is located within the bore 332 and in designed to travel along the threaded section 335. In one embodiment, the urging member 375 is in the form of an urging screw that is located within the bore. The urging screw 375 has external threads that are complementary to the threaded section 335 and therefore, the urging screw 375 threadingly mates with and travels along the threaded section. The urging screw 375 thus has a complementary shape relative to the bore 332 and in particular, the threaded section 335 and therefore, in one embodiment, the urging screw 375 has a circular or hexagonal shape.

The gear section 380 can be formed at one end of the pin 310. The gear section 380 is intended to act as a gear to permit rotation of the pin 310 relative to the sleeve 400 as described below. The gear section 380 has a size and shape that is complementary to the shape and size of the bore 410 formed in the sleeve. In the illustrated embodiment, the gear section 380 has a cylindrical shape and includes a flared flange (annular flange) 385 formed at the end 314 of the pin 310. An outer surface of the gear section 380 serves as a gear and accordingly, the outer surface of the gear section 380 is defined by a plurality of teeth 382. The teeth 382 are defined by a plurality of spaced, vertically oriented ribs that extend about the circumference of the gear section 380. Along with a side wall of the pin, the flange 385 includes the teeth 382. The flange 385 thus represents a slotted annular flange.

The teeth 382 are configured to mate with the coupling element 420 of the sleeve 400. In particular, the dimensions (width) of the coupling element 420 are about equal to the spacing between the teeth 382 and therefore, the coupling element 420 is intimately received within the spacing between the teeth 382. When first inserting the pin 310 into the sleeve, the two rails 420 are aligned and guided into respective spaces between teeth 382 of the flange 385. It will be appreciated that the outer peripheral edge of the flange 385 contacts and seats against the inner surface of the bore 410 of the sleeve 400. The flange 385 serves to stabilize the pin 310 within the bore 410 of the sleeve 400.

The materials used to form the teeth 382 and the coupling elements 420 are resilient enough that when the coupling elements 420 are received within the space between adjacent teeth 382 and the pin 300 is rotated relative to the fixed sleeve 400, the pin 300 moves a predetermined amount due to the teeth 382 moving relative to the fixed coupling elements (rail) 420. An audible "click" can be heard to indicate that the pin 300 has moved one rotational position.

In one embodiment, the spacing of the teeth 382 and the dimensions of the rails 420 are such that one rotation of the pin 310 results in a 2° rotation of the pin 310 relative to the sleeve 400. It will be appreciated that due to the close proximity of adjacent teeth in a patient's jaw, during the course of a normal orthodontic treatment, a tooth is unlikely to be rotated more than 16°. It will be understood that the above incremental degrees of change are merely exemplary and the teeth can be configured so that each rotation results in a different degree of change. As a result, the gear section 380 can be formed to only include 8 incremental rotational movements. In other words, the teeth 382 do not have to be formed around the entire circumference but can be limited to less than the entire circumference to limit the degree of rotational movement of the pin 310 relative to the sleeve 400. The number of teeth 382 can be limited so that the pin 310 cannot be rotated more than, say, 16° relative to the sleeve 400.

Since the tooth anchor section is fixedly attached to tooth die, rotation of the tooth die is directly translated into rotation of the pin 310 relative to the sleeve 400.

Since the rails 420 extends the entire length of the bore 410 of the sleeve 400, the pin 310 is inserted into the bore 410 by aligning the rail 420 with one space formed between the teeth 382 and then slidingly moving the pin 310 within the bore 410 of the sleeve 400 until the gear section 380 is located at or near the end of the sleeve 400 to permit access to the bore 332 formed in the pin 310 at the end of the sleeve 400. In other arrangements the teeth 382 can be located intermediate the ends of the pin 310. Also the teeth can comprise recesses that cooperate with complementary structure within the bone 410 of the sleeve 400.

As with conventional dowel pins, the sleeve 400 is fixedly attached to the base of the model and the individual tooth dies are simply removably coupled to the base by inserting the pin 310 into the sleeve 400. FIG. 3 shows the base 270 including a combination of conventional sleeves 280 and sleeves 400 made in accordance with the present invention. In this manner, the sleeves 280 receive standard dowel pins, while the sleeves 400 are used with the pins 310 of the present invention that are designed to allow the tooth die to be moved by the orthodontist to a new position.

Figure 5A:
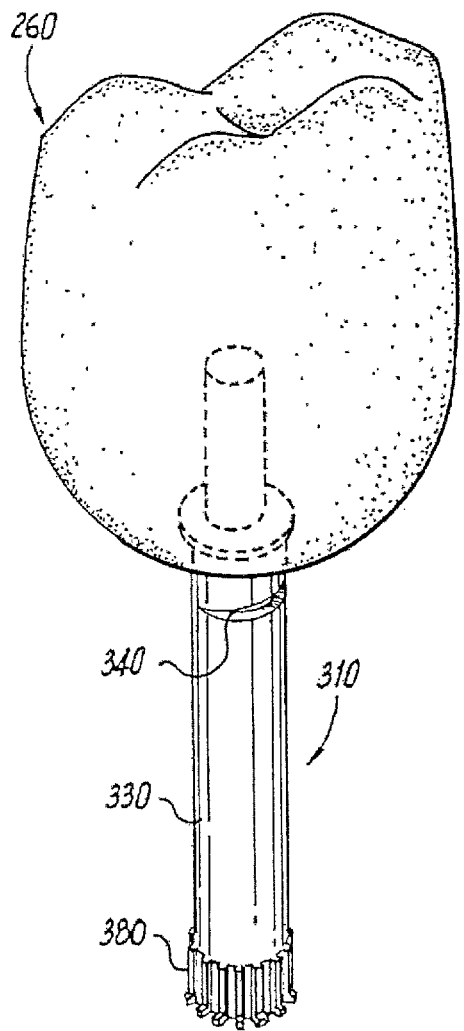
FIG. 5A shows the dowel pin fixedly attached to a tooth die with the living hinge in a first orientation relative to the tooth die.
Figure 5B:
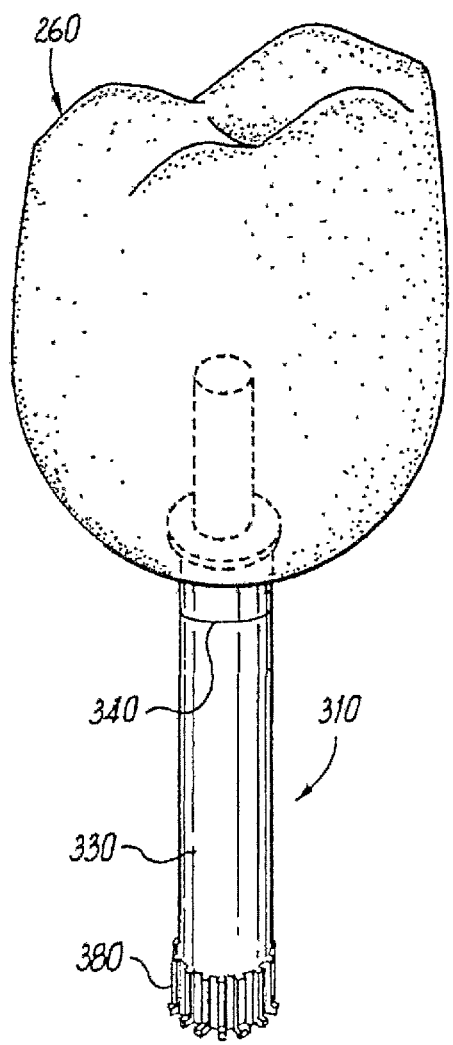
FIG. 5B shows the dowel pin fixedly attached to a tooth die with the living hinge in a first orientation relative to the tooth die.

The operation of the assembly 300 is now described. Once the tooth anchor section 320 is fixedly attached to the tooth die, the tooth die can be moved in a number of different directions by manipulation of the assembly 300. For example and as shown in FIG. 1, if it desired to move the tooth die in one or more directions indicated in FIG. 1 (e.g., a forward/rearward movement of the tooth), the pin 310 is fixedly attached to the tooth die such that the living hinge 340 opens in this same direction as the desired movement of the tooth die. If the tooth die is desired to move in left-to-right movement, then the pin 310 is simply attached to the tooth die with the living hinge 340 opening in this left-to-right direction. It will therefore be appreciated that the tooth die can be moved in any number of different directions to accommodate the tooth movements that are normally encountered in orthodontic treatments. FIGS. 5A and 5B shows two different orientations of the pin 310 relative to the tooth die 260. In particular, FIG. 5A shows the living hinge 340 oriented to open in a right-to left manner as shown in the figure sheet, while FIG. 5B shows the hinge 340 opening in direction out of the page of the drawing sheet. Advantageously, after adjustment of the tooth die, it remains in the new position which allows a new aligner to be created.

A tool 500 is provided for engaging the urging screw 375. For example, a small Allen wrench type tool can be provided for insertion into the bore 332 and for mating with the urging screw 375. Rotation of the tool 500 causes rotation of the urging screw 375 resulting in the urging screw traveling along the threaded section 362 (whether the urging screw is driven toward or away from the tooth die depends on which direction the tool is rotated). To cause movement of the tooth dire, the urging screw 375 is driven along the threaded section 362 until the urging screw 375 enters the slot 342 of the living hinge 340 and comes into contact with the underside of the first part 344 that is located above the slot 344. It will be appreciated that continued movement of the urging screw 375 caused an upward force to be applied to the first part 344 and since the first part 344 is connected to the second part 346 by means of the living hinge 340, the first pivot 344 pivots about the living hinge 340 resulting in a pivoting of the tooth die that is attached to the tooth anchor 320 (which is directly connected to the first part 344).

The degree to which the urging screw 375 is driven into the slot 342 depends upon the degree of pivoting in the tooth die that is desired. Thus, depending upon the degree of intended movement of the tooth die, the urging screw is driven a certain amount into contact with the In other words, the angle that the hinge 340 opens correlates to the degree of movement of the tooth die. If the tooth die is only intended to pivot a small amount as in the case with a patient that only needs minor correction of the tooth position, then the living hinge 340 is only opened a small amount. Conversely, if the patient's tooth requires more severe movement, then the urging screw is driven to a greater degree to cause the living hinge 340 to open to a greater degree. The degree that the hinge 340 opens is controlled with precision by using the tool 500 to cause the urging screw to open the hinge 340 to the desired degree. If the hinge 340 is opened too much, the orthodontist simply has to rotate the tool in the opposite direction to cause the urging screw to back away from the first part 342.

It will further be appreciate that the tooth die can be rotated a predetermined number of degrees by simply grasping the tooth die and slowly rotating it until it assumes the desired position. Controlled rotation of the tooth die is made possible due to the coupling between the rail 420 and the gear section 380 and the resulting controlled rotation of the pin 310 relative to the sleeve 400. Audible clicking noises will be heard as the pin 310 is rotated.

As a result, the tooth die can be adjusted according to a number of different degrees of freedom using the pin assembly 300 of the present invention in place of a conventional dowel pin.

It will be appreciated that the pin 300 can be formed according to conventional techniques, such as injection molding using molds. When injection molding is used, the urging member (urging screw) 375 is disposed within the mold and the pin structure is formed therearound. As a result, the urging member 375 is located within the bore 332. In addition, the tool 500 can be disposed within the mold so as to form a lower portion of the bore 332.

As a result of incorporating the pin assembly 300 into one or more of the tooth dies, the tooth dies that form a part of the model can be manually manipulated by the orthodontist to suggest and formulate an orthodontic treatment plan for a particular patient. As described above, by first setting the living hinge 420 in the correct position relative to the tooth die, the tooth die can be moved in increments until the tooth die assumes its final, desired position.

The sleeve 400 is fixedly attached to the base using conventional techniques and in one embodiment, the base is formed around the strategically placed sleeves 400. For example, the material that forms the base is introduced into a mold that has the sleeves 400 positioned therein. The material flows around the sleeves 400 and thus when it hardens, the sleeves 400 are securely held within the base at their proper locations.

FIG. 6 shows one exemplary pin assembly 390 in an exploded manner The pin assembly 390 is similar to the pin assembly 300. However, in the pin assembly 390, the gear section 380 does not include a flared flange at its end and instead, the gear section 380 is simply defined by a plurality of teeth (in the form of fingers) that are defined by spaced slots formed circumferentially about the gear section 380. One tooth or finger is defined between a pair of slots. It will be appreciated that the outer diameters of the main body section and the gear section 380 are equal.

The sleeve 400 includes a complementary locking rail or wedge 495 that is formed along the inner surface of the bore 410 at the end of the sleeve 400. The locking rail 495 is sized and shaped so as to lockingly engage one space between adjacent teeth 382 as described above with reference to pin assembly 300.

As shown in FIG. 6, the pin assembly 300 can include a plug 450 that is constructed to intimately mate with the sleeve 400. The plug 450 has a post portion 452 and a base portion 454 with the post portion 452 extending outwardly from the base portion 454. The post portion 452 can be a hollow cylindrical shaped structure (e.g., a tube). The plug 450 (post portion 452) is inserted into the bore 410 of the sleeve 400. The plug 450 can be formed of any number of different materials including but not limited to polymeric materials and rubber. For example, the plug 450 can be in the form of a rubber plug (stopper) that is inserted into the bore 410 of the sleeve 400 to close off the sleeve 400. It is desirable to close off the bore 410 of the sleeve 400 during the formation of the base 270 when the base 270 is formed since it is not desirable for the material that forms the base 270 to enter the bore 410. If this material enters the bore 410 and hardens, it will obstruct the bore 410 and the operation of the pin.

The sleeve 400 also includes an extension 415 that extends beyond the end of the sleeve 400. The extension 415 has a tubular shape with a bore 417 that is axially aligned with the bore 415. In one embodiment, the bores 410 and 417 have substantially similar or identical inner diameters. The extension 415 is designed to receive the post portion 452 of the plug 450. It will be appreciated that absent this extension 415, the insertion of the plug 450 into the sleeve 410 will be prevented due to the presence of the rail/wedge 495. The length of the extension 415 is thus approximately the same length of the post portion 452 of the plug 450.

Figure 7:
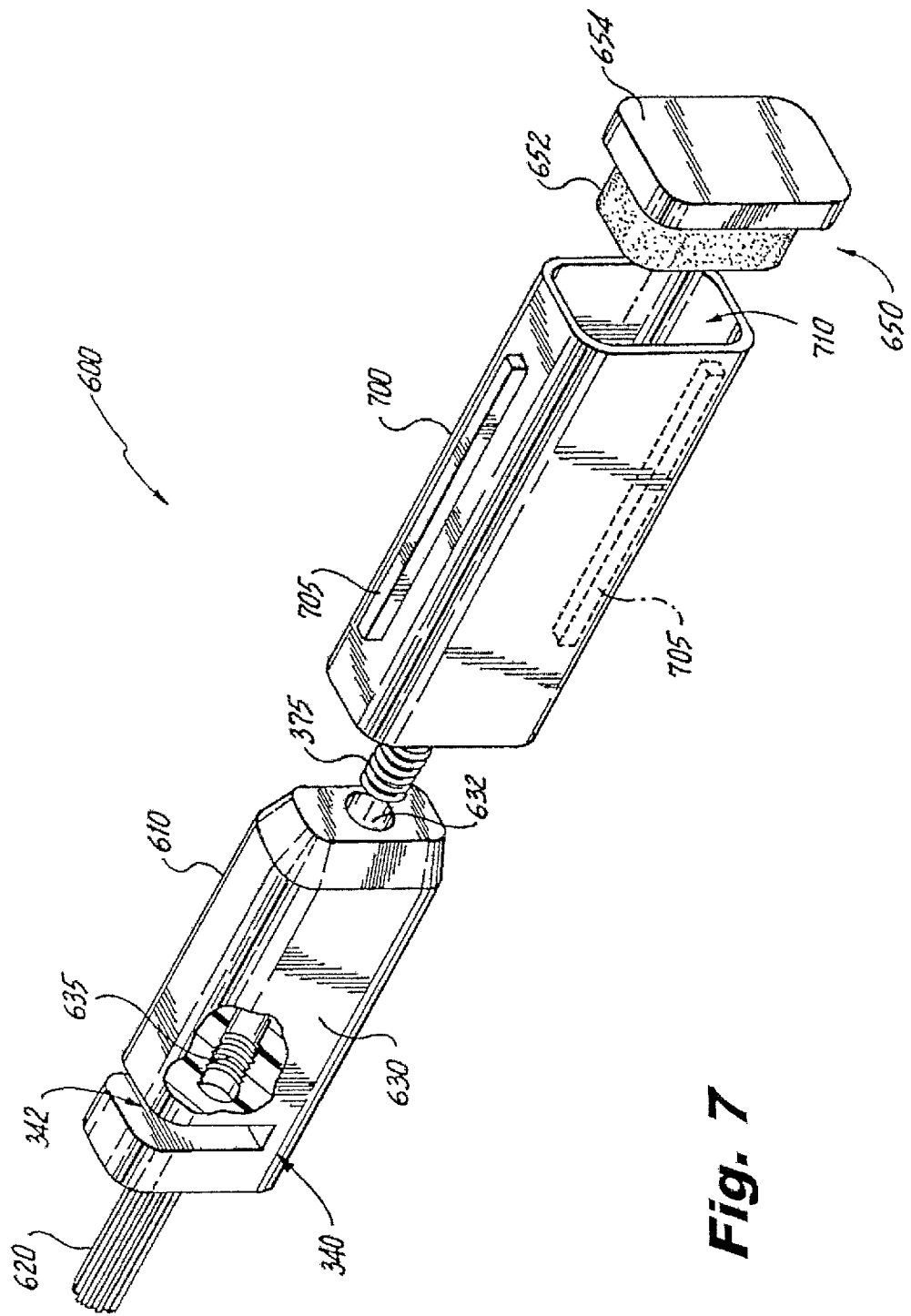
FIG. 7 is an exploded view of an exemplary dowel pin assembly according to another embodiment.

FIG. 7 illustrates a pin assembly 600 according to another embodiment of the present invention. The pin assembly 600 is similar to the pin assembly 300. One difference between the pin assembly 600 and the pin assembly 300 is that in the pin assembly 600, the pin itself is not controllably rotated as in the pin assembly 300. The pin assembly 600 is formed of a pin 610 and a sleeve 700. The pin 610 is similar to pin 310 and includes a tooth anchor portion 620 and a main body portion 630. The tooth anchor portion 620 is identical or similar to the tooth anchor portion 320. The main body portion 630 is similar to the main body portion 330. The main body portion 630 has a bore 632 formed therein with a threaded section 635. Living hinge 340 is formed therein and defined by slot 342. Urging member 375 is disposed within the bore 632 and threadingly engages the threaded section 635. Unlike the pin assembly 300, the pin 610 has no gear section.

The sleeve 700 is similar to the sleeve 400 and includes a hollow interior 710. The sleeve 700 can also include one or more features 705 that serve to locate and fix/anchor the sleeve 700 within the base 270. As discussed above, the base 270 is formed around the sleeve 700 that are fixed in place in their proper locations so that the pins attached to the dowel pins are aligned therewith. For example, the sleeve 700 includes a pair of opposing rails 705 that are formed along the outer surface of the sleeve 700. The rails 705 do not extend along the entire length of the sleeve 700. The rails 705 serve to anchor the sleeve 700 within the base.

The pin assembly 600 also includes a plug 650 that is constructed to intimately mate with the sleeve 700. The plug 650 has a post portion 652 and a base portion 654 with the post portion 652 extending outwardly from the base portion 654. The post portion 652 can be a hollow cylindrical shaped structure (e.g., a tube). The plug 650 (post portion 652) is inserted into the bore 710 of the sleeve 700. The plug 650 can be formed of any number of different materials including but not limited to polymeric materials and rubber. For example, the plug 650 can be in the form of a rubber plug (stopper) that is inserted into the bore 710 of the sleeve 700 to close off the sleeve 700. It is desirable to close off the bore 710 of the sleeve 700 during the formation of the base 270 when the base 270 is formed since it is not desirable for the material that forms the base 270 to enter the bore 710. If this material enters the bore 710 and hardens, it will obstruct the bore 710 and the operation of the pin. In use, the plug 650 can easily be removed.

The use of the present model for the formation of the plurality of aligners to cause the patient's teeth to move from the initial tooth arrangement to the final tooth arrangement is now described. More specifically, the orthodontist has a great amount of discretion in the customization of the orthodontic treatment plan for a particular patient since the orthodontist can make proposed adjustments to one or more tooth dies by manipulating the respective pin assemblies 300 to cause the desired movements of the respective tooth dies.

There is a significant cost savings using the present invention since the adjustments that are made using the assembly of the present invention can be made by conventional heat-forming technique without computer controlled machines on site. The better interaction with a patient by showing the patient corrective ships steps on a material 3-D model instead of a computer screen. In other words, the personal dentist can work with his or her own patient in developing and personally illustrating the proposed treatment plan. This is a significant advantage since the patient will better appreciate the course of treatment when it is shown before their very eyes in a physical 3-D model. Planning every next step based on a real progress taking into account the actual patient's response to the adjustments, etc., as opposed to charter an entire course of treatment as is done in the prior art systems. Since the system and method of the present invention is customizable, the course of treatment can be changed mid treatment if the patient is making more or less progress than anticipated.

After moving the respective tooth dies from the initial tooth arrangement to a first tooth arrangement, the model is then used in the formation of a unique aligner. To form the aligner, the model is inserted into a vacuum forming system. The vacuum forming system has a compartment that has a platform that receives the model. Surrounding the model is a plurality of vacuum apertures or the like which cause a vacuum to be established in the compartment. The platform on which the model rests is often called a vacuum plate. The system includes a heating unit that includes a heating element. The heating unit is typically rotatable and is spaced from the platform. The vacuum forming system has a frame that includes the platform and has a hinged frame part that receives a sheet of vacuum forming material. The hinged frame part is closed and secured with a frame latch, thereby positioning the sheet of vacuum forming material over the model. The heating unit is then swung into position squarely over the sheet of vacuum forming material and at this time, the vacuum is on. The plastic vacuum forming material heats quickly and begins to soften and the vacuum forming material flows over the model (tooth dies).

A suitable vacuum forming system is commercially available from Buffalo Dental under the trade name Sta-Vac II. The Sta-Vac II uses a heating element other than a laser and therefore, unlike the Invisalign® system, vacuum forming materials of greater thickness can be used. As previously mentioned, the Invisalign® system uses a laser light vacuum forming system and therefore, a thin sheet of vacuum forming material is required to be used due to the heating properties and capabilities of the laser.

The vacuum forming system is then turned off and after a sufficient cooling period, the formed aligner is removed and can be cut to remove fringe material, etc., thereby leaving behind an aligner (polymeric shell) that is fabricated for placement over the patient's teeth. As described above, the aligner applied a resilient repositioning force against the tooth or teeth to be repositioned.

The patient's teeth are repositioned from their initial tooth arrangement to an intermediate and/or final tooth arrangement by placing a series of incremental aligners over the patient's teeth. To form the next aligner for use by the patient, the orthodontist simply manually manipulates the tooth die(s) that requires further repositioning and thereby causes adjustment of the respective pin assembly 300. Once the proper tooth arrangement is achieved, the orthodontist repeats the process and places the adjusted model into the vacuum forming system. The vacuum forming system is operated, as described above, a new aligner is formed.

The above process is repeated until the desired number of aligners is formed. Unlike the conventional processes, a treatment plan using the aligners of the present invention is more customizable and the length of treatment can be reduced since the thicker aligners can be used and therefore, more aggressive incremental changes can be realized.

It will be appreciated that the pin assembly 300 according to the present invention permits the model of the patient's teeth to be interactive in that the orthodontist can manipulate individual tooth dies until the tooth die assumes a desired tooth arrangement that includes an incremental change relative to the prior tooth arrangement. The degree and magnitude of the incremental tooth change is left up to the individual orthodontist. As a result, the orthodontist can customize and tailor the treatment plan to a particular patient and not be limited by parameters, such as the thickness of the aligner due to the starting thickness of the sheet of vacuum forming material.

It will be appreciated that there are other manners of interlockingly mating the pin 310 with the sleeve 410. For example, the outer surface of the main body section 330 can include a plurality of rings that are formed of spaced bumps or projections. The spacing between the bumps represents the degree of rotation for one rotational movement of the pin 310 within the sleeve 400. In this embodiment, the bumps can form circumferential rings or they can form partial circumferential rings. The sleeve 400 is formed with complementary rings of openings, with each opening being sized to receive one bump. Thus, when the pin 310 is inserted into the sleeve bore 410, the bumps ride along the inner surface of the sleeve 400 until they are aligned with complementary openings at which time, the bumps are received into the openings, thereby lockingly coupling the two together. When controlled and precise rotation of the pin 310 relative to the sleeve 400 is desired, the tooth die and thus, the pin 310 is rotated causing the bumps to disengage one set of openings and the subsequently engage the adjacent set of openings that all are formed in the same ring structure. This results in a controlled rotation of the pin 310 within and relative to the sleeve 400.

While the invention has been described in connection with certain embodiments thereof, the invention is capable of being practiced in other forms and using other materials and structures. Accordingly, the invention is defined by the recitations in the claims appended hereto and equivalents thereof.

What is claimed is:

1. A manually adjustable physical 3-D model that has a plurality of tooth dies, wherein at least one tooth die can be selectively adjusted to a new position to allow formation of an aligner that is intended to be worn on teeth of the patient comprising:
   a first model part that is formed of a plurality of tooth dies;
   a second model part complementary to the first model part and being in the form of a base on which the first part rests; and
   a dowel pin and sleeve combination for use with the tooth die that is intended to be adjusted, the combination comprising:
      a dowel pin including:
         a tooth anchor section that is configured to be fixedly attached to the tooth die;
         a main body section having a bore formed therein and open at one end of the pin, the main body section having a slot that defines a living hinge formed therein that partitions the main body section into an upper pivotable portion that pivots about the hinge and a lower portion, wherein a section of the bore is threaded and the main body section includes an urging member that travels along the threaded bore section and can be driven into contact with the pivotable portion of the main body section, the bore forming an entrance into the slot that defines the living hinge to permit the urging member to be driven into contact with the pivotable portion,
         wherein the sleeve includes a longitudinal locating and locking rail formed along an outer surface thereof for locating and fixing the sleeve within a corresponding opening formed in the base;
   wherein the tooth die is pivotable about the living hinge and is prevented from rotating relative to the sleeve.

2. A dowel pin for use with a tooth die that is part of a dental model comprising:
   a tooth anchor section that is configured to be fixedly attached to the tooth die;
   a main body section having a bore formed therein and open at one end of the pin, the main body section having a slot that defines a living hinge formed therein that partitions the main body section into an upper pivotable portion that pivots about the hinge and a lower portion, wherein a section of the bore is threaded and the main body section includes an urging member that travels along the threaded bore section and can be driven into contact with the pivotable portion of the main body section, the bore forming an entrance into the slot that defines the living hinge to permit the urging member to be driven into contact with the pivotable portion to cause adjustment of a position of the tooth die relative to the pin; and
   a sleeve that has a central bore formed therein that is configured to receive the main body section.

3. The dowel pin of claim 2, wherein the tooth anchor section comprise a post and has an outer surface that is modified to promote improved fixation between the tooth anchor section and the tooth die.

4. The dowel pin of claim 3, where a width of the tooth anchor section is less than a width of the adjoining main body section resulting in a shoulder being formed therebetween.

5. The dowel pin of claim 3, wherein the urging member comprises a screw that has external threads that are complementary to the threaded bore section.

6. The dowel pin of claim 2, wherein the pin is formed of a plastic material.

7. The dowel pin of claim 2, wherein the sleeve includes at least one longitudinal locating and locking rail formed along an outer surface of the sleeve, the rail being configured for locking the sleeve within a base of a tooth die model.

8. The dowel pin of claim 7, wherein there are a pair of locking rails located on opposite outer surfaces of the sleeve.

9. The dowel pin of claim 7, wherein the sleeve has a rectangular shape.

10. The dowel pin of claim 2, further including a plug that is received within one end of the sleeve for sealingly closing off the central bore formed in the sleeve.

11. The dowel pin of claim 10, wherein the plug includes a base and a post having reduced size compared to the base, the post being received within the central bore.

12. The dowel pin of claim 2, wherein the sleeve is open and both ends thereof for allowing a tool to be inserted into the bore of the main body section and into contact with the urging member.

13. The dowel pin of claim 2, wherein the bore is only formed in the lower portion of the main body section.

* * * * *